(12) United States Patent
Hartley et al.

(10) Patent No.: US 9,011,517 B2
(45) Date of Patent: Apr. 21, 2015

(54) SIDE BRANCH STENT GRAFT

(75) Inventors: David Ernest Hartley, Wannanup (AU); Werner Dieter Ducke, Greenwood (AU); Chantelle King, Subiaco (AU); Blayne A. Roeder, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 220 days.

(21) Appl. No.: 12/912,175

(22) Filed: Oct. 26, 2010

(65) Prior Publication Data

US 2011/0313512 A1 Dec. 22, 2011

(30) Foreign Application Priority Data

Jun. 18, 2010 (AU) .................................. 2010202544

(51) Int. Cl.
*A61F 2/06* (2013.01)
*A61F 2/07* (2013.01)
*A61F 2/89* (2013.01)

(52) U.S. Cl.
CPC ... *A61F 2/07* (2013.01); *A61F 2/89* (2013.01); *A61F 2002/061* (2013.01); *A61F 2220/0075* (2013.01)

(58) Field of Classification Search
CPC ........................................................ A61F 2/07
USPC ........................................................ 623/1.35
See application file for complete search history.

(56) References Cited

U.S. PATENT DOCUMENTS

| | | | | |
|---|---|---|---|---|
| 4,309,776 A | * | 1/1982 | Berguer ........................ | 623/1.41 |
| 6,187,033 B1 | * | 2/2001 | Schmitt et al. ............... | 623/1.35 |
| 6,478,817 B2 | * | 11/2002 | Schmitt et al. ............... | 623/1.35 |
| 6,520,988 B1 | * | 2/2003 | Colombo et al. ............ | 623/1.35 |
| 7,645,298 B2 | | 1/2010 | Hartley et al. | |
| 2003/0033008 A1 | * | 2/2003 | Schmitt et al. ............... | 623/1.51 |
| 2003/0199967 A1 | * | 10/2003 | Hartley et al. ............... | 623/1.13 |
| 2005/0059923 A1 | * | 3/2005 | Gamboa .......................... | 604/9 |
| 2005/0131517 A1 | * | 6/2005 | Hartley et al. ............... | 623/1.13 |

(Continued)

FOREIGN PATENT DOCUMENTS

EP 1847234 B1 7/2009
WO 2005/034809 A1 4/2005

(Continued)

OTHER PUBLICATIONS

PCT/US2010/054067 International Search Report and Written Opinion, Wm. A. Cook Australia Pty. Ltd., Jan. 18, 2011.

*Primary Examiner* — Jacqueline Woznicki
(74) *Attorney, Agent, or Firm* — Brinks Gilson & Lione

(57) ABSTRACT

A stent graft has a tubular side arm which can be angled proximally and distally and from side to side. The wall of the stent graft in the vicinity of the side arm has a loose fold of the graft material and the side arm is fastened to the loose fold of graft material. The tubular side arm has an inner end and an outer end and is fastened into the loose fold of graft material by a circumferential fastening around the tubular side arm between the inner end and the outer end so that the tubular side arm extends partially within the tubular body of the stent graft and partially outside the tubular body of the stent graft. The loose fold of graft material can be formed by the graft material defining a recess in the wall of the stent graft. To enable movement or angulation proximally and distally and from side to side the loose fold of graft material is provided both proximally and distally of the tubular side arm and circumferentially to each side of the tubular side arm.

14 Claims, 6 Drawing Sheets

(56) References Cited

U.S. PATENT DOCUMENTS

| | | | |
|---|---|---|---|
| 2006/0155366 A1* | 7/2006 | LaDuca et al. | 623/1.23 |
| 2006/0217796 A1* | 9/2006 | DiMatteo et al. | 623/1.16 |
| 2007/0055360 A1* | 3/2007 | Hanson et al. | 623/1.35 |
| 2007/0219621 A1 | 9/2007 | Hartley et al. | |
| 2009/0093873 A1* | 4/2009 | Navia | 623/1.23 |
| 2010/0057186 A1* | 3/2010 | West et al. | 623/1.13 |
| 2010/0268327 A1* | 10/2010 | Bruszewski et al. | 623/1.18 |

FOREIGN PATENT DOCUMENTS

| | | |
|---|---|---|
| WO | 2008/021557 A1 | 2/2008 |
| WO | 2008/057568 A1 | 5/2008 |
| WO | 2008/062405 A2 | 5/2008 |
| WO | 2009/104000 A1 | 8/2009 |
| WO | 2010/024849 A1 | 3/2010 |
| WO | 2010/024879 A1 | 3/2010 |

* cited by examiner

SIDE BRANCH STENT GRAFT

TECHNICAL FIELD

This disclosure relates to a medical device and more particularly to a stent graft deployed by endovascular techniques.

BACKGROUND OF THE INVENTION

In recent years endovascular implantable devices have been developed for treatment of aortic aneurysms. These devices are delivered to the treatment site through the vascular system of the patient rather than by open surgery. The devices include a tubular or cylindrical framework or scaffolding of one or more stents to which is secured a tubular shape of graft material such as woven Dacron, polyester polytetrafluoroethylene or the like. The devices are initially reduced to a small diameter, placed into the leading or proximal end of a catheter delivery system. The delivery system is inserted into the vascular system of the patient such as through a femoral incision. The leading end of the delivery system is maneuvered to the treatment site over a previously positioned guide wire. Through manipulation of a control system that extends to the proximal end of the catheter from the distal end of the system outside the patient the implantable device is then deployed by holding the device as its location and withdrawing a surrounding sheath. The stent graft or implantable device can then self expand or is expanded through the use of a balloon which is introduced with the stent graft implantable device. The stent graft becomes anchored into position to healthy wall tissue in the aorta after which the delivery system is removed leaving the device in position thereby bypassing an aneurysm in the aorta in a manner that channels all blood flow through the stent graft so that no blood flow enters the aneurysm, such that not only does the aneurysm no longer continue to grow and possibly rupture but the aneurysm actually begins to shrink and commonly disappears entirely.

Where there are branch vessels from the aorta then provision may need to be made to supply blood to the branch vessels. This is done by fenestrations and where necessary side branch extension stent grafts.

This disclosure will be generally discussed in relation to treatment of aortic aneurysms in the thoraco-abdominal region of the aorta but the disclosure is not so limited and can be used where there are branch vessels from a main vessel.

For treatment of thoracic aortic aneurysms in particular it is necessary to introduce the implantable device high up in the aorta and in a region of the aorta which is curved and where there can be strong blood flow.

In the thoracic aorta there are major branch vessels, the brachiocephalic, the left carotid and the left subclavian and for treatment of an aneurysm in the region of the thoracic arch provision must be made for blood supply to continue to these arteries while an operation is in progress and after completion of the operation. For this purpose fenestrations or side branches are provided into a stent graft in that region. Access is generally obtained to these fenestrations to deploy side arms into the stent graft via the left or right brachial arteries or less commonly via the left or right carotid arteries.

Catheterisation of a branch vessel from a main vessel can be difficult and to assist pre-catheterised fenestrations or side branches have been used.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form the disclosure is said to reside in a stent graft comprising a tubular body comprising a wall of a biocompatible graft material and at least one tubular side arm received in the wall, the wall in the vicinity of the side arm comprising a loose fold of the graft material, the side arm being fastened to the loose fold of graft material such that the tubular side arm can be angled proximally and distally and from side to side.

Preferably the tubular side arm comprises an inner end and an outer end and is fastened into the loose fold of graft material by a circumferential fastening around the tubular side arm between the inner end and the outer end.

Preferably the tubular side arm extends partially within the tubular body of the stent graft and partially outside the tubular body of the stent graft.

Preferably the tubular side arm comprises a reinforcing ring at each end thereof and a plurality of zig zag reinforcing struts extending between the reinforcing rings.

Preferably the loose fold of graft material is provided proximally and distally of the tubular side arm and the side arm can be angled proximally and distally. Alternatively the loose fold of graft material can be provided circumferentially to each side of the tubular side arm and the side arm can be angled laterally or from side to side. Alternatively the loose fold of graft material is provided both proximally and distally of the tubular side arm and circumferentially to each side of the tubular side arm and the side arm can be angled proximally and distally and angled laterally from side to side.

In an alternative form the disclosure comprises a stent graft comprising a tubular body comprising a wall of a biocompatible graft material, the tubular body being supported by a plurality of zig zag stents, a portion of graft material between two adjacent stents of the plurality of zig zag stents comprising a loose fold region of the graft material, and at least one tubular side arm received in the loose fold region of the graft material, the side arm being fastened to the loose fold of graft material such that the loose fold of material is proximally and distally of the tubular side arm and wherein the tubular side arm can be angled proximally and distally.

In an alternative form the disclosure comprises a stent graft comprising a tubular body comprising a wall of a biocompatible graft material, the tubular body being supported by a plurality of zig zag stents, a portion of graft material between two adjacent stents of the plurality of zig zag stents comprising a loose fold region of the graft material, and at least one tubular side arm received in the loose fold region of the graft material, the side arm being fastened to the loose fold of graft material such that the loose fold of material is provided circumferentially to each side of the tubular side arm and the side arm can be angled laterally from side to side.

In an alternative form the disclosure comprises a stent graft comprising a tubular body comprising a wall of a biocompatible graft material, the tubular body being supported by a plurality of zig zag stents, a portion of graft material between two adjacent stents of the plurality of zig zag stents comprising a loose fold region of the graft material, and at least one tubular side arm received in the loose fold region of the graft material, the side arm being fastened to the loose fold of graft material such that the loose fold of material is provided both proximally and distally of the tubular side arm and circumferentially to each side of the tubular side arm and the side arm can be angled proximally and distally and angled laterally from side to side.

In an alternative form the disclosure comprises a stent graft comprising;
   a tubular body defining a main lumen therethrough, a plurality of zig zag stents along the tubular body, each of the stents comprising a plurality of struts and bends, the bends being between adjacent struts;
   at least a first stent and an adjacent second stent, the first and second stents having at least a pair of adjacent bends on the first stent aligned with an adjacent pair of bends on the second stent, whereby a first pair of adjacent struts of the first stent and a second pair of adjacent struts of the second adjacent stent together define a diamond shaped region;
   a recess in the diamond shaped region, the recess extending into the lumen of the tubular body, the recess being defined by a recess portion of a biocompatible graft material;
   a tubular side arm extending from and in fluid communication with the tubular body within the recess, the tubular side arm comprising an inner end and an outer end being fastened into the recess portion of graft material within the diamond shaped region by a circumferential fastening around the tubular side arm between the inner end and the outer end, such that the tubular side arm can be angled at least one of proximally and distally and from side to side.

In this embodiment of the disclosure the recess portion of the biocompatible graft material provides a loose fold of the biocompatible graft material around the tubular side arm.

Preferably the stent graft further comprises a third adjacent stent, the third adjacent stent having at least a pair of bends adjacent to the second stent whereby a third pair of adjacent stents of the third strut defines a second diamond shaped region,
   wherein the second diamond shaped region shares a strut with the first diamond shaped region,
   a second recess in the second diamond shaped region, the second recess extending into the lumen of the tubular body, the second recess being defined by a second recess portion of a biocompatible graft material;
   a second tubular side arm extending from and in fluid communication with the tubular body within the second recess, the second tubular side arm comprising an inner end and an outer end being fastened into the second recess portion of graft material within the second diamond shaped region by a circumferential fastening around the second tubular side arm between the inner end and the outer end, such that the second tubular side arm can be angled proximally and distally and from side to side.

In an alternative form the disclosure comprises a stent graft comprising a tubular body comprising a wall of a biocompatible graft material and at least one tubular side arm received in the wall, the tubular side arm comprising an inner end and an outer end, the wall in the vicinity of the side arm comprising a loose fold of the graft material when the side arm is extending substantially at right angles to the tubular body of the stent graft, the tubular side arm being fastened to the loose fold of graft material by a circumferential fastening around the tubular side arm between the inner end and the outer end such that the tubular side arm can be angled proximally at its outer end wherein to facilitate cathertisation of a branch vessel and distally at is outer end wherein to facilitate placement of a side arm extension stent graft and the tubular side arm remaining in its proximal or distal position without tension in the previously loose fold of graft material unless acted upon by an external force.

In an alternative form the disclosure comprises a stent graft comprising a tubular body comprising a wall of a biocompatible graft material and at least one tubular side arm received in the wall, the wall in the vicinity of the side arm comprising sufficient graft material such that the tubular side arm can be angled proximally to a proximal position and distally to a distal position without inducing sufficient tension in the graft material that would otherwise bias the tubular side arm away from the respective proximal and distal positions.

BRIEF DESCRIPTION OF THE DRAWING

This then generally describes the disclosure but to assist with understanding reference will now be made to the accompanying drawings which show preferred embodiments of the disclosure.

In the drawings.

DETAILED DESCRIPTION

Figure 1:
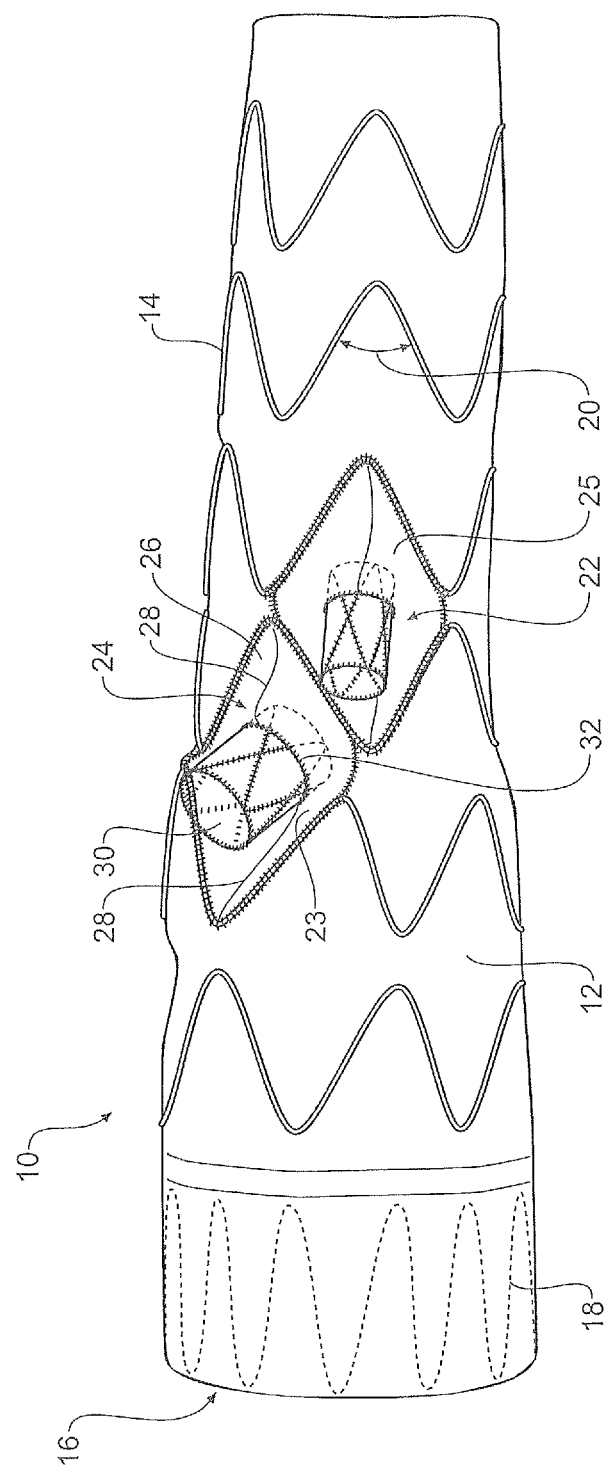
FIG. 1 shows a stent graft being a first embodiment of the present disclosure.
Figure 2:
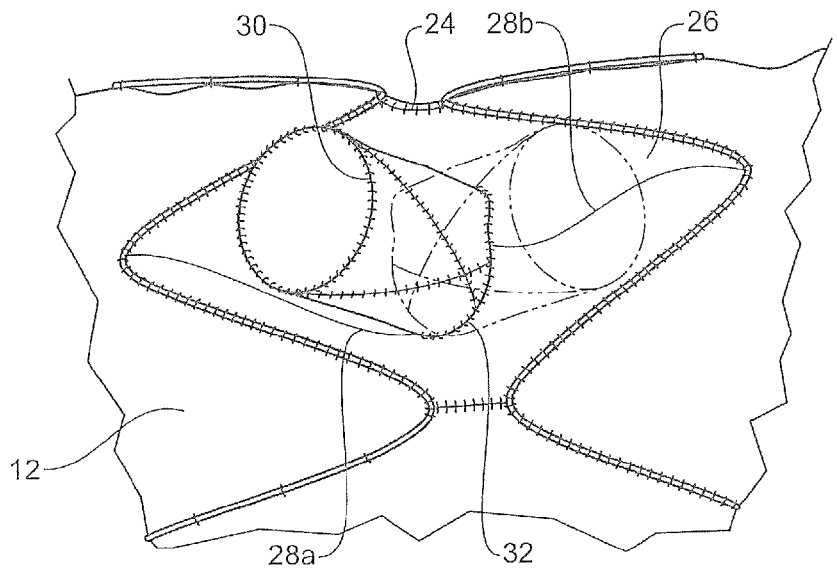
FIG. 2 shows detail of the stent graft of FIG. 1.

FIG. 1 shows a stent graft being a first embodiment of the present disclosure and FIG. 2 shows a detail of a portion of the stent graft shown in FIG. 1.

In FIG. 1 a stent graft 10 comprises a tubular body 12 of a biocompatible graft material. The stent graft is supported by a number of zig zag stents 14 which extend along the length of the tubular body 12 and at a proximal end 16 there is an internal zig zag stent 18 thereby providing on the outside of the stent graft a sealing surface to engage the wall of a vessel within the vasculature of a patient.

In this embodiment the zig zag stents 14 are formed from nitinol and therefore have a relatively wide included angle 20 such that a pair of stents, where the points of the stents align, form substantially diamond shaped regions 22 and 24.

Into each of the regions 22 and 24 a recess 25, 23 respectively is formed and lined or defined by graft material 26 to form the recess. The graft material 26 includes folded regions 28 which are adjacent to a tubular side arm 30 which is received into the recess and stitched as at 32 into the recess.

As can be seen particularly in FIG. 2 the loose material 28a to the proximal side of the side arm 30 and the loose material 28b to the distal side of the side arm 30 enables the side arm to be angled or toggled or oriented proximately or distally or to point to one side or the other of the stent graft. The advantage of having a side arm extending from a stent graft which can be angled proximately or distally or from side to side will be discussed in detail in relation to FIGS. 5 and 6.

Figure 3A:
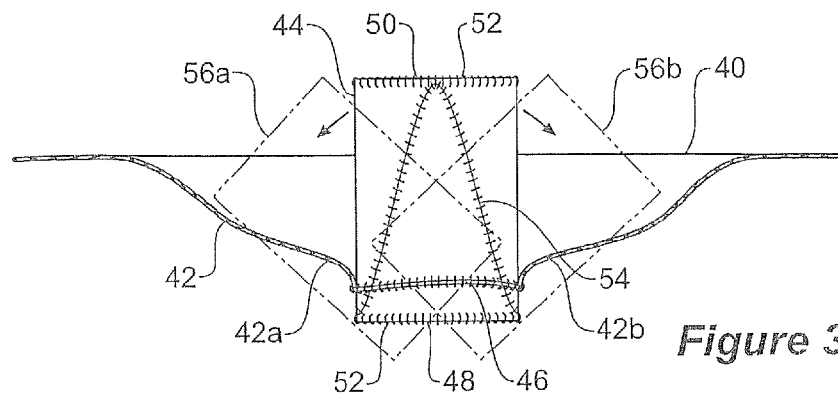
FIGS. 3A to 3C show schematically a first embodiment of the present disclosure.
Figure 3B:
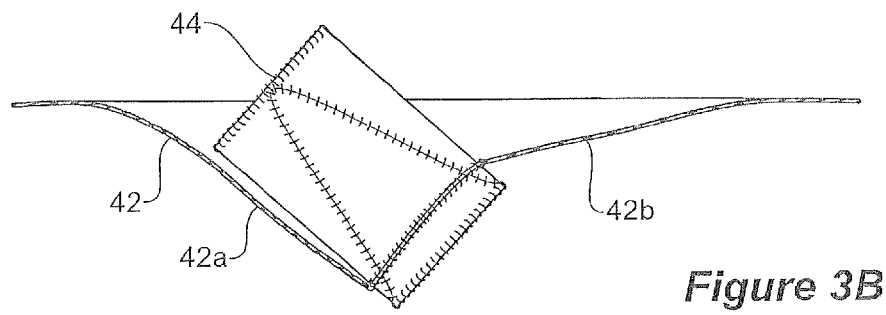
Figure 3C:
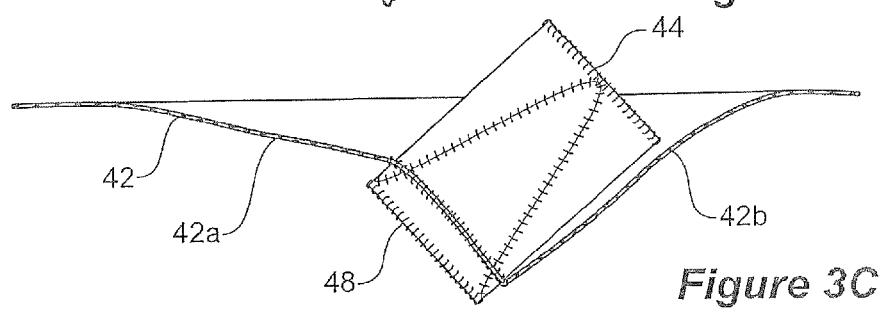

FIGS. 3A to 3C show schematically a first embodiment of the present disclosure.

In FIG. 3A, a wall 40 of a stent graft includes a formed recess 42 and a tubular side arm 44 is stitched into the recess by a circumferential stitching 46 which is between the inner end 48 and the outer end 50 of the tubular side arm 44. As shown in FIG. 3A, the perimeters of the inner end 48 and outer end 50 are free of attachment to the wall 40 of the stent graft such that the tubular side arm 44 can be manipulated intraluminally.

In this embodiment the tubular side arm 44 includes a reinforcing ring 52 at each end and a zig zag stent reinforcement 54 between the ends.

Immediately to each side of the side arm 44 there is a loose fold of the material of the recess 42a and 42b and this loose fold enables the tubular side arm to be angled as shown by the dotted lines 56a and 56b.

The arrangement angled to 56a is shown in FIG. 3B. The side arm 44 is angled such that both the folds 42a and 42b of the biocompatible graft material 42 forming the recess are at least partially tightened and the side arm 44 is angled to one side in this case proximately at its outer end and distally at its inner end, that is, within the tubular body of the stent graft.

The arrangement of the angled side arm at 56b is shown in FIG. 3C. In this embodiment again the folds 42a and 42b have been at least partially tightened by the side arm 44 being angled so that the outer end is angled to one side in this case distally and the inner end 48 is directed to a proximal end.

The existence of the loose fold of material to each side of the tubular side arm when it is in the position extending substantially at right angles to the stent graft means that when the tubular side arm is toggled or angled to one side or the other, the side arm stays in the toggled or angled position without the previously loose folds being tensioned to the extent that they provide a returning force. If an external force is applied such as by a guide wire passing through the side arm then the side arm can be toggled or angles to an different position.

Figure 4A:
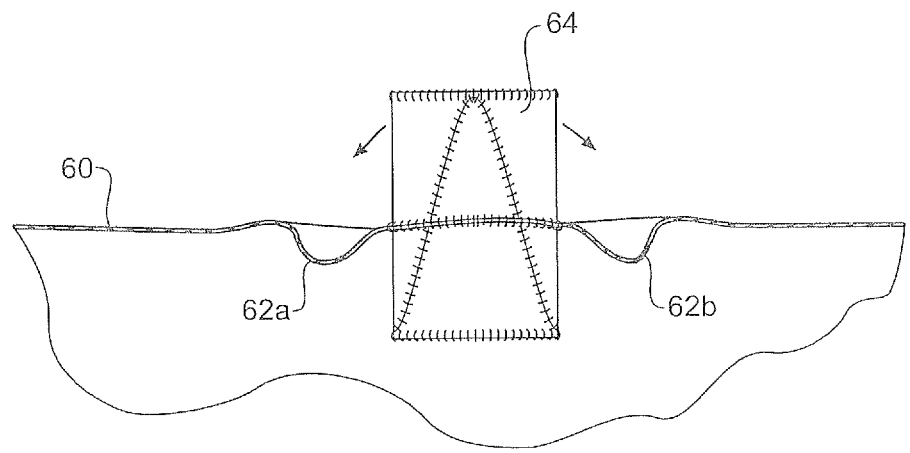
FIGS. 4A to 4C show schematically a second embodiment of the present disclosure.
Figure 4B:
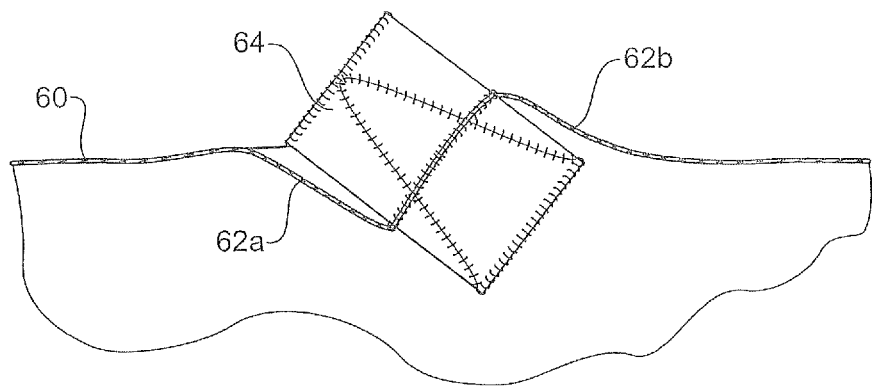
Figure 4C:
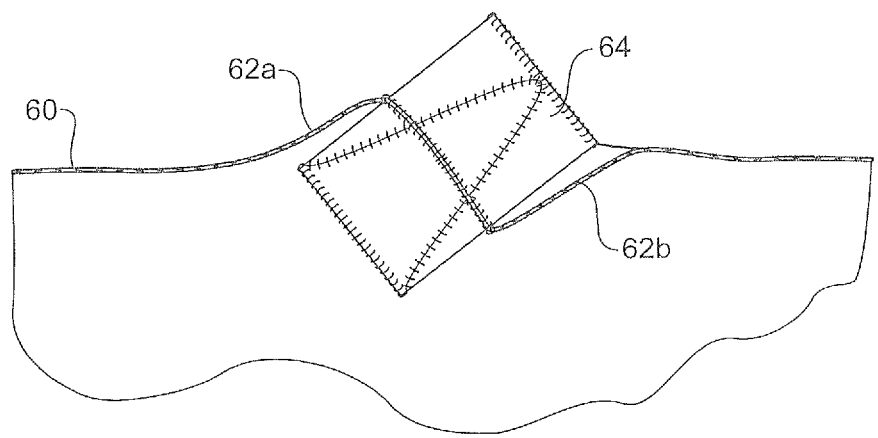

FIGS. 4A to 4C show an alternative embodiment in which the loose fold of cloth which enables the tubular side arm to be directed approximately or distally or from side to side is provided in the surface of the tubular body rather than within a recess in the tubular body. In this embodiment the tubular body of a stent graft has a wall 60 which is formed into loose fold 62a and 62b either side of a tubular side arm 64. The loose fold can also be positioned proximally or distally and/or from side to side so that the side arm can be oriented at any desired angle.

As can be seen in FIG. 4B when the tubular side arm 64 is angled to one side both the loose folds 62a and 62b are tightened up but the angling of the side arm is allowed. Similarly in FIG. 4C the tubular side arm 64 is angled to the other side and the folds 62a and 62b are tightened up.

Figure 5:
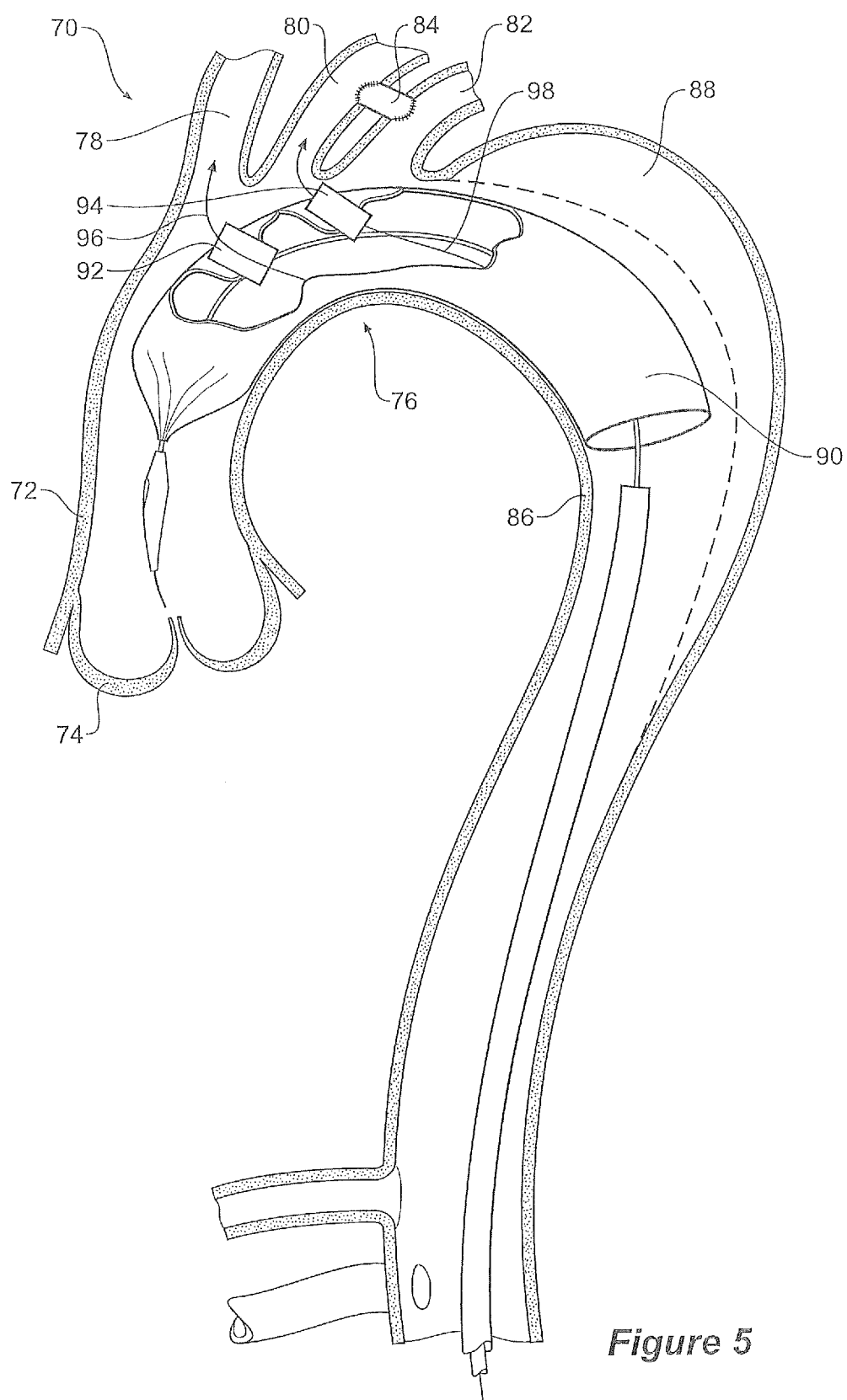
FIG. 5 shows a schematic view of a first stage of the deployment of a stent graft incorporating the present disclosure into a thoracic arch.
Figure 6:
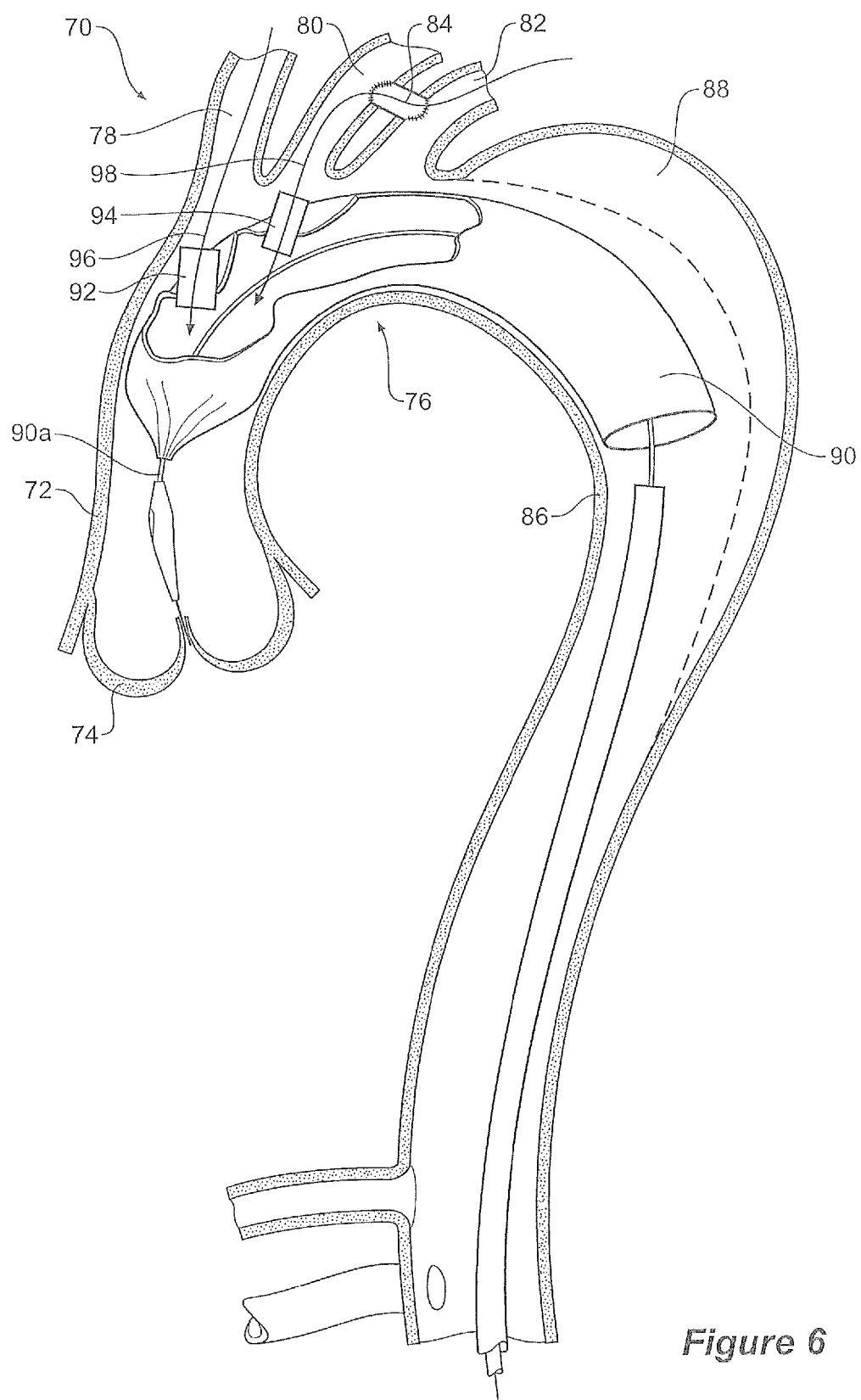
FIG. 6 shows a schematic view of a later stage of the deployment of a stent graft incorporating the present disclosure into a thoracic arch.

FIGS. 5 and 6 show a schematic view of the thoracic aorta of a patient and in particular a thoracic aorta with an aortic aneurism adjacent to the great vessels of the thoracic arch. In such an arrangement it is usually not possible to land a endovascularly placed stent graft distally of the great vessels as there is not sufficient landing zone to seal a stent graft against and hence it is necessary to deploy a stent graft which has a sealing surface proximately of the great vessels and therefore requires side branches to supply blood flow to the great vessels.

The schematically illustrated thoracic arch 70 includes an ascending aorta 72 ascending from an aortic valve 74 of the heart up to a thoracic arch 76 from which extends the brachiocephalic artery 78, the left common carotid artery 80 and the left subclavian artery 82. Generally when providing side branches into these arteries an anastomosis is provided between the left carotid artery and the left subclavian artery as shown as 84 and two side arms are used. The aorta has a descending aorta portion 86 which has an aneurism 88.

A particular problem that exists with catheterization of the great vessels and deploying side arms from the great vessels into a stent graft is to obtain access from a partially deployed stent graft into those vessel. In FIG. 5 a schematic drawing showing a partially deployed stent graft 90 is illustrated. In this stent graft side arms according to the present disclosure 92 and 94 are provided. In the schematic arrangement as shown in FIG. 5 the side arms are toggled or angled so that their inner ends face distally within the tubular body of the stent graft 90 and this enables catheterization through them into the brachiocephalic artery 78 and left common carotid artery 80 as shown by the arrows 96 and 98 respectively.

Once catheterization has occurred the stent graft can be further advanced so that its proximal end 90a extends further down the ascending aorta 72. At this stage the guide wires 96 and 98 that have been used for catheterization of the side arms 92 and 94 or further guide wires replacing them can be used to deploy side branch extensions and in doing this the side arms 92 and 94 can be angled so that their outer ends can extend distally which facilitates the placement of the side arm stent graft extension and which facilitates blood flow into the vessels after they have been grafted.

Figure 7:
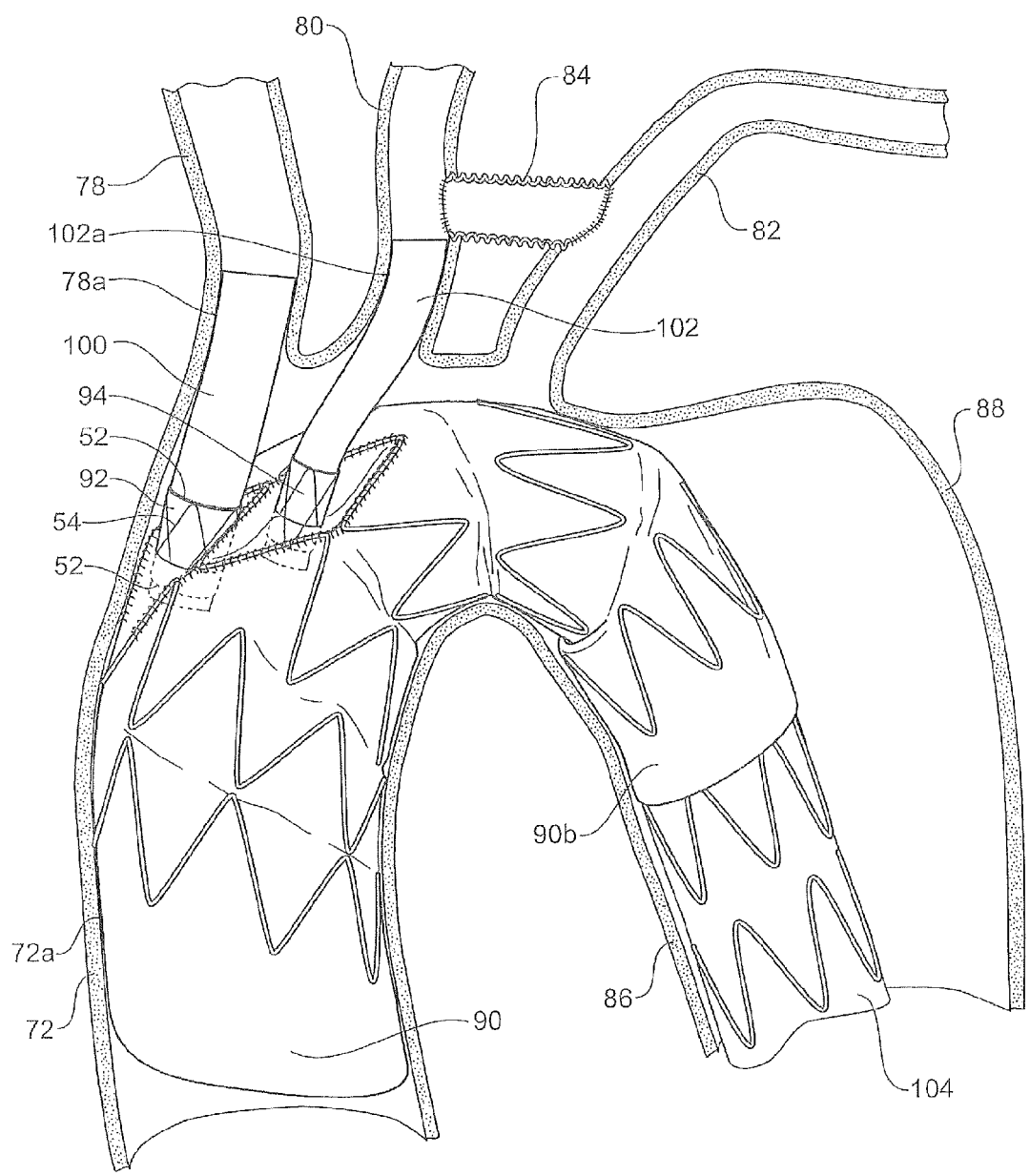
FIG. 7 shows a schematic view of a final stage of the deployment of a stent graft incorporating the present disclosure into a thoracic arch.

FIG. 7 shows the result of the arrangement as discussed in relation to FIGS. 5 and 6. The stent graft 90 is sealed into the ascending aorta 72 at 72a and a first side branch stent graft 100 is deployed through the brachiocephalic artery 78 into the side arm 92 to seal into the brachiocephalic artery 78 at 78a. At this stage the side arm 92 is toggled so that its outer end extends distally. The side arm 94 has received a side arm stent graft 102 from the left common carotid artery 80 and seals into the left common carotid artery at 102a. The anastomosis 84 also allows for perfusion of the left subclavian artery 82. Again the side arm 94 is extended distally at its outer end.

The reinforcing rings 52 and the zig zag stent 54 on the side arm stent graft enable a good seal to be obtained between a side arm stent graft and the respective side branches.

The distal end 90b of the stent graft extends down the descending aorta 86 and into the aneurism 88 and hence a further stent graft 104 has been deployed to provide a seal at the other end of the aneurism 88 (not shown).

It can be seen that by this disclosure there is provided an arrangement by which a side arm of a stent graft can be toggled in one direction for instance for facilitating catheterization and into another direction to facilitate alignment with a side branch vessel.

Although the disclosure has generally been discussed in relation to the thoracic arch and to proximal or distal angulations of the side arm it will be realized that the arrangement can be used in other side branch situations in the aorta or other vessels of the human or animal body and can be angled from side to side to facilitate alignment with other side branch vessels such as the renal arteries the celiac artery or the mesenteric arteries.

Throughout the specification various indications have been given as to the scope of the disclosure but the disclosure is not limited to any one of these but may reside in two or more combined together. Examples are given for illustration only and not for limitation.

What is claimed is:

1. A stent graft having a delivery configuration prior to introduction into a body vessel, the stent graft comprising a tubular body comprising a wall of a biocompatible graft material and at least one tubular side arm received in the wall, and having a first free end and a second free end, the wall in the vicinity of the side arm comprising a loose fold of the graft material, the side arm being fastened to the loose fold of graft material in the delivery configuration such that the tubular side arm can be angled proximally and distally and from side to side, wherein the tubular side arm comprises an inner end having a perimeter and an outer end having a perimeter and is fastened into the loose fold of graft material by a circumferential fastening element around the tubular side arm between the inner end and the outer end whereby the tubular side arm extends partially inwardly and partially outwardly from the circumferential fastening, within the tubular body of the stent graft and partially outside the tubular body of the stent graft, wherein the perimeters of the first free end and the second free end are free of attachment to the wall of the tubular body such that the tubular side arm can be manipulated intraluminally from a position angled proximally to a position angled distally.

2. A stent graft as in claim 1 wherein the tubular side arm comprises a reinforcing ring at each end thereof and a plurality of zig zag reinforcing struts extending between the reinforcing rings.

3. A stent graft as in claim 1 wherein the loose fold of graft material is provided proximally and distally of the tubular side arm and the side arm can be angled proximally and distally.

4. A stent graft as in claim 1 wherein the loose fold of graft material is provided circumferentially to each side of the tubular side arm and the side arm can be angled laterally from side to side.

5. A stent graft as in claim 1 wherein the loose fold of graft material is provided both proximally and distally of the tubular side arm and circumferentially to each side of the tubular side arm and the side arm can be angled proximally and distally and angled laterally from side to side.

6. A stent graft having a delivery configuration prior to introduction into a body vessel, the stent graft comprising a tubular body comprising a wall of a biocompatible graft material, the tubular body being supported by a plurality of zig zag stents, a portion of graft material between two adjacent stents of the plurality of zig zag stents comprising a loose fold region of the graft material, and at least one tubular side arm having a first free end having a perimeter and second free end having a perimeter, received in the loose fold region of the graft material, the side arm being fastened to the loose fold of graft material in the delivery configuration such that the loose fold of material is proximally and distally of the tubular side arm and wherein the tubular side arm can be angled proximally and distally, wherein the tubular side arm comprises an inner end and an outer end and is fastened into the loose fold region of graft material by a circumferential fastening element around the tubular side arm between the inner end and the outer end whereby the tubular side arm extends partially inwardly and partially outwardly from the circumferential fastening, within the tubular body of the stent graft and partially outside the tubular body of the stent graft, wherein the perimeters of the first free end and the second free end are free of attachment to the wall of the tubular body such that the tubular side arm can be manipulated intraluminally from a position angled proximally to a position angled distally.

7. A stent graft as in claim 6 wherein the circumferential fastening element comprises stitching through both the tubular side arm and the loose fold region about a circumference of the tubular side arm.

8. A stent graft as in claim 6 wherein the tubular side arm comprises a reinforcing ring at each end thereof and a plurality of zig zag reinforcing struts extending between the reinforcing rings.

9. A stent graft having a delivery configuration prior to introduction into a body vessel, the stent graft comprising a tubular body comprising a wall of a biocompatible graft material, the tubular body being supported by a plurality of zig zag stents, a portion of graft material between two adjacent stents of the plurality of zig zag stents comprising a loose fold region of the graft material, and at least one tubular side arm, having a first free end having a perimeter and a second free end having a perimeter, received in the loose fold region of the graft material, the side arm being fastened to the loose fold of graft material in the delivery configuration such that the loose fold of material is provided circumferentially to each side of the tubular side arm and the side arm can be angled laterally from side to side, wherein the tubular side arm comprises an inner end and an outer end and is fastened into the loose fold region of graft material by a circumferential fastening element around the tubular side arm between the inner end and the outer end whereby the tubular side arm extends partially inwardly and partially outwardly from the circumferential fastening, wherein the tubular body of the stent graft and partially outside the tubular body of the stent graft, wherein the perimeters of the first free end and the second free end are free of attachment to the wall of the tubular body such that the tubular side arm can be manipulated intraluminally from a position angled proximally to a position angled distally.

10. A stent graft having a delivery configuration prior to introduction into a body vessel, the stent graft comprising a tubular body comprising a wall of a biocompatible graft material, the tubular body being supported by a plurality of zig zag stents, a portion of graft material between two adjacent stents of the plurality of zig zag stents comprising a loose fold region of the graft material, and at least one tubular side arm, having a first free end and a second free end, received in the loose fold region of the graft material, the side arm being fastened to the loose fold of graft material in the delivery configuration such that the loose fold of material is provided both proximally and distally of the tubular side arm and circumferentially to each side of the tubular side arm and the side arm can be angled proximally and distally and angled laterally from side to side, wherein the tubular side arm comprises an inner end and an outer end and is fastened into the loose fold region of graft material by a circumferential fastening element around the tubular side arm between the inner end and the outer end whereby the tubular side arm extends partially inwardly and partially outwardly from the circumferential fastening element, within the tubular body of the stent graft and partially outside the tubular body of the stent graft, wherein the first free end and the second free end are free of attachment to the wall of the tubular body such that the tubular side arm can be manipulated intraluminally from a position angled proximally to a position angled distally.

11. A stent graft having a delivery configuration prior to introduction into a body vessel, the stent graft comprising:
a tubular body defining a main lumen therethrough, a plurality of zig zag stents along the tubular body, each of the stents comprising a plurality of struts and bends, the bends being between adjacent struts;
at least a first stent and an adjacent second stent, the first and second stents having at least a pair of adjacent bends on the first stent aligned with an adjacent pair of bends on the second stent, whereby a first pair of adjacent struts of the first stent and a second pair of adjacent struts of the second adjacent stent together define a diamond shaped region;

a recess in the diamond shaped region, the recess extending into the lumen of the tubular body, the recess being defined by a recess portion of a biocompatible graft material; and a tubular side arm extending from and in fluid communication with the tubular body within the recess, the tubular side arm having an inner end having a perimeter and an outer end having a perimeter, the tubular body being fastened into the recess portion of graft material in the delivery configuration within the diamond shaped region by a circumferential fastening element around the tubular side arm between the inner end and the outer end, such that the tubular side arm can be angled at least one of proximally and distally and from side to side, whereby the tubular side arm extends partially inwardly and partially outwardly from the circumferential fastening element, within the perimeters of the inner end and the outer end are free of attachment wall of the tubular body such that the tubular side arm can be manipulated intraluminally from a position angled proximally to a position angled distally.

12. A stent graft as in claim 11 further comprising a third adjacent stent, the third adjacent stent having at least a pair of bends adjacent to the second stent whereby a third pair of adjacent stents of the third strut defines a second diamond shaped region;

wherein the second diamond shaped region shares a strut with the first diamond shaped region;

a second recess in the second diamond shaped region, the second recess extending into the lumen of the tubular body, the second recess being defined by a second recess portion of a biocompatible graft material; and a second tubular side arm extending from and in fluid communication with the tubular body within the second recess, the second tubular side arm comprising an inner end and an outer end being fastened into the second recess portion of graft material within the second diamond shaped region by a circumferential fastening element around the second tubular side arm between the inner end and the outer end, such that the second tubular side arm can be angled proximally and distally and from side to side and whereby the tubular side arm extends partially inwardly and partially outwardly from the circumferential fastening element, within the tubular body of the stent graft and partially outside the tubular body of the stent graft,such that the tubular side arm can be manipulated intraluminally from a position angled proximally to a position angled distally.

13. A stent graft having a delivery configuration prior to introduction into a body vessel, the stent graft comprising a tubular body comprising a wall of a biocompatible graft material and at least one tubular side arm received in the wall, the tubular side arm comprising an inner end having a perimeter and an outer end having a perimeter, the wall in the vicinity of the side arm comprising a fold of the graft material, the fold of the graft material being loose when the side arm is extending substantially at right angles to the tubular body of the stent graft, the tubular side arm being fastened to the loose fold of graft material in the delivery configuration by a circumferential fastening element around the tubular side arm between the inner end and the outer end such that the tubular side arm can be angled proximally at its outer end wherein to facilitate cathertisation of a branch vessel and distally at is outer end wherein to facilitate placement of a side arm extension stent graft and the tubular side arm remaining in its proximal or distal position without tension in the previously loose fold of graft material unless acted upon by an external force whereby the tubular side arm extends partially inwardly and partially outwardly from the circumferential fastening element, and has an inner end and an outer end, within the tubular body of the stent graft and partially outside the tubular body of the stent graft, wherein the perimeters of the inner end and the outer end are free of attachment to the wall of the tubular body such that the tubular side arm can be manipulated intraluminally from a position angled proximally to a position angled distally.

14. A stent graft having a delivery configuration prior to introduction into a body vessel, the stent graft comprising a tubular body comprising a wall of a biocompatible graft material and at least one tubular side arm received in the wall, the wall in the vicinity of the side arm comprising sufficient graft material such that the tubular side arm can be angled proximally to a proximal position and distally to a distal position without inducing sufficient tension in the graft material that would otherwise bias the tubular side arm away from the respective proximal and distal positions, wherein the tubular side arm comprises an inner end having a perimeter and an outer end having a perimeter and is fastened into the loose fold region of graft material in the delivery configuration by a circumferential fastening element around the tubular side arm between the inner end and the outer end whereby the tubular side arm extends partially inwardly and partially outwardly from the circumferential fastening element, within the tubular body of the stent graft and partially outside the tubular body of the stent graft, wherein the perimeters of the inner end and the outer end are free of attachment to the wall of the tubular body such that the tubular side arm can be manipulated intraluminally from a position angled proximally to a position angled distally.

* * * * *

UNITED STATES PATENT AND TRADEMARK OFFICE
CERTIFICATE OF CORRECTION

PATENT NO.         : 9,011,517 B2
APPLICATION NO.    : 12/912175
DATED              : April 21, 2015
INVENTOR(S)        : David Ernest Hartley et al.

Page 1 of 1

It is certified that error appears in the above-identified patent and that said Letters Patent is hereby corrected as shown below:

In the Claims

In column 7, claim 6, line 45, immediately after "one tubular side arm" insert --,--.

In column 7, claim 6, line 46, after "a perimeter and" insert --a--.

In column 8, claim 9, line 25, after "fastening," replace "wherein" with --within--.

In column 9, claim 11, line 20, before "perimeters of the inner" insert --tubular body of the stent graft and partially outside the tubular body of the stent graft, wherein the--.

Signed and Sealed this
Fifteenth Day of September, 2015

Michelle K. Lee
*Director of the United States Patent and Trademark Office*